US00PP22220P2

(12) United States Plant Patent
Castanet

(10) Patent No.: US PP22,220 P2
(45) Date of Patent: Nov. 1, 2011

(54) BARBERRY PLANT NAMED 'REDTORCH'

(50) Latin Name: *Berberis thunbergii*
Varietal Denomination: Redtorch

(75) Inventor: Christian-Maurice Castanet, Allassac (FR)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 12/924,018

(22) Filed: Sep. 17, 2010

(51) Int. Cl.
*A01H 5/00* (2006.01)

(52) U.S. Cl. ..... Plt./241

(58) Field of Classification Search ..... Plt./241
See application file for complete search history.

*Primary Examiner* — Kent L Bell

(74) *Attorney, Agent, or Firm* — C. A. Whealy

(57) ABSTRACT

A new and distinct cultivar of *Barberry* plant named 'Redtorch', characterized by its narrow and upright plant habit; leaves that are dark purple in color and in the autumn become bright red in color; and tolerance to Powdery Mildew.

2 Drawing Sheets

Botanical designation: *Berberis thunbergii.*
Cultivar denomination: 'REDTORCH'.

BACKGROUND OF THE INVENTION

The present invention relates to a new and distinct cultivar of *Barberry* plant, botanically known as *Berberis thunbergii* and hereinafter referred to by the name 'Redtorch'.

The new *Barberry* plant is a product of a planned breeding program conducted by the Inventor in Allassac, France. The objective of the breeding program was to develop new erect *Barberry* plants with attractive foliage.

The new *Barberry* plant originated from an open-pollination in 2002 of an unnamed selection of *Barberry thunbergii*, not patented, as the female, or seed parent and an unknown selection of *Barberry thunbergii* as the male, or pollen, parent. The new *Barberry* plant was discovered and selected by the Inventor in 2003 as a single plant within the progeny of the stated open-pollination in a controlled environment in Allassac, France.

Asexual reproduction of the new *Barberry* plant by softwood cuttings in a controlled greenhouse environment in Beaufort-en-Vallée, France since the Jun. 1, 2004 has shown that the unique features of this new *Barberry* plant are stable and reproduced true to type in successive generations of asexual reproduction.

SUMMARY OF THE INVENTION

Plants of the new *Barberry* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Redtorch'. These characteristics in combination distinguish 'Redtorch' as a new and distinct cultivar of *Barberry* plant:

1. Narrow and upright plant habit.
2. Leaves that are dark purple in color and in the autumn become bright red in color.
3. Tolerant to Powdery Mildew.

Plants of the new *Barberry* can be compared to plants of the female parent selection. Plants of the new *Barberry* differ from plants of the female parent selection in the following characteristics:

1. Plants of the new *Barberry* are more erect than plants of the female parent selection.
2. Developing leaves of the new *Barberry* are more red in color than developing leaves of the female parent selection.
3. Plants of the new *Barberry* have healthier and more durable leaves than plants of the female parent selection.

Plants of the new *Barberry* can be compared to plants of the *Berberis thunbergii* 'Helmond Pillar', not patented. In side-by-side comparisons conducted in Beaufort-en-Vallée, France, plants of the new *Barberry* differed from plants of 'Helmond Pillar' in the following characteristics:

1. Plants of the new *Barberry* were more vigorous than plants of 'Helmond Pillar'.
2. Leaves of plants of the new *Barberry* were more red in color than leaves of plants of 'Helmond Pillar'.
3. During the autumn, leaves of plants of the new *Barberry* were red in color whereas leaves of plants of 'Helmond Pillar' were purple in color.

BRIEF DESCRIPTION OF THE PHOTOGRAPHS

The accompanying colored photographs illustrate the overall appearance of the new *Barberry* plant showing the colors as true as it is reasonably possible to obtain in colored reproductions of this type.

Colors in the photographs may differ slightly from the color values cited in the detailed botanical description which accurately describe the colors of the new *Barberry* plant.

The photograph on the first sheet is a side perspective view of a typical plant of 'Redtorch' grown during the autumn in an outdoor nursery.

The photograph on the second sheet is a close-up view of a typical plant of 'Redtorch' in the autumn.

DETAILED BOTANICAL DESCRIPTION

The aforementioned photographs and following observations, measurements and values describe plants grown during the late autumn in an outdoor nursery in Beaufort-en-Valée, France and under conditions which closely approximate commercial production. During the production of the plants, day temperatures ranged from 6° C. to 20° C. and night temperatures ranged from 1° C. to 15° C. Plants were three years old when the photographs and the description were taken. In the description, color references are made to The Royal Horticultural Society Colour Chart, 2007 Edition, except where general terms of ordinary dictionary significance are used.

Botanical classification: *Berberis thunbergii* 'Redtorch'.

Parentage:

*Female, or seed, parent.*—Unnamed selection of *Barberry thunbergii*, not patented.

*Male, or pollen, parent.*—Unknown selection of *Barberry thunbergii*, not patented.

Propagation:

*Type.*—By softwood cuttings.

*Time to initiate roots, summer.*—About 30 days at 20° C.

*Time to produce a rooted young plant, summer.*—About three months at 18° C.

*Root description.*—Fine, fleshy; yellow in color.

*Rooting habit.*—Moderate branching; sparse.

Plant description:

*Plant form and growth habit.*—Perennial shrub; narrow and upright plant habit; moderately vigorous to vigorous growth habit.

*Branching habit.*—Moderate branching habit, about 38 lateral branches develop per plant; pruning will enhance lateral branch development.

*Plant height.*—About 73.8 cm.

*Plant diameter* (*area of spread*).—About 28.5 cm.

Lateral branch description:

*Length.*—About 34.1 cm.

*Diameter.*—About 2 mm.

*Internode length.*—About 1.1 cm.

*Aspect.*—Mostly upright.

*Texture.*—Smooth, glabrous.

*Color, young.*—Close to 200C to 200D.

*Color, fully developed.*—Close to 199D with longitudinal stripes, close to 200A.

*Thorns.*—Quantity/arrangement: About one at each node. Length: About 9 mm. Width: About 0.7 mm. Color: Close to 165A.

Foliage description:

*Arrangement.*—Alternate, simple.

*Length.*—About 2.1 cm.

*Width.*—About 1 cm.

*Shape.*—Obovate.

*Apex.*—Rounded to abruptly acute.

*Base.*—Attenuate.

*Margin.*—Entire.

*Texture, upper and lower surfaces.*—Smooth, glabrous.

*Venation pattern.*—Pinnate.

*Color.*—Developing leaves, upper surface: Close to N186C. Developing leaves, lower surface: Close to 177C to 177D tinged with close to 182C. Fully expanded leaves, upper surface: Between N186C and 200B; venation, between N186C and 200B; in the autumn, color becomes closer to 46A. Fully expanded leaves, lower surface: Close to 177C to 177D tinged with close to 182C; venation, close to 187D.

*Petiole.*—Length: About 5 mm. Diameter: About 0.7 mm. Texture, upper and lower surfaces: Smooth, glabrous. Color, upper surface: Between N186C and 200B. Color, lower surface: Close to 187D.

Flower description: Flower initiation and development has not been observed on plants of the new *Barberry*.

Garden performance: Plants of the new *Barberry* have been observed to have excellent garden performance and to tolerate rain, wind and temperatures ranging from about −20° C. to about 40° C.

Pathogen/pest tolerance: Plants of the new *Barberry* have been observed to be tolerant to Powdery Mildew (*Oidium* sp.). Plants of the new *Barberry* have not been shown to be tolerant to pests and other pathogens common to *Barberry* plants.

It is claimed:

1. A new and distinct *Barberry* plant named 'Redtorch' as illustrated and described.

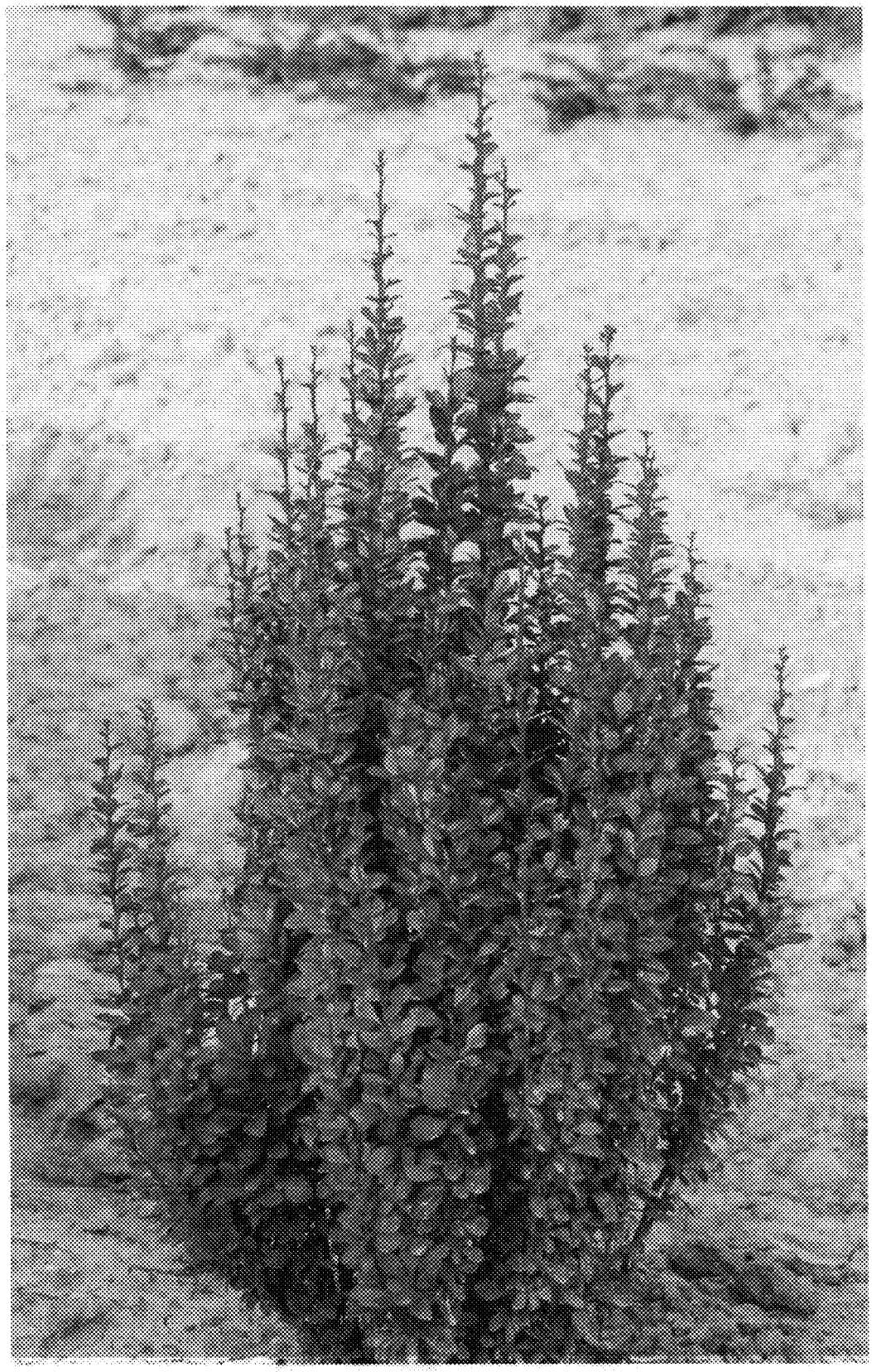

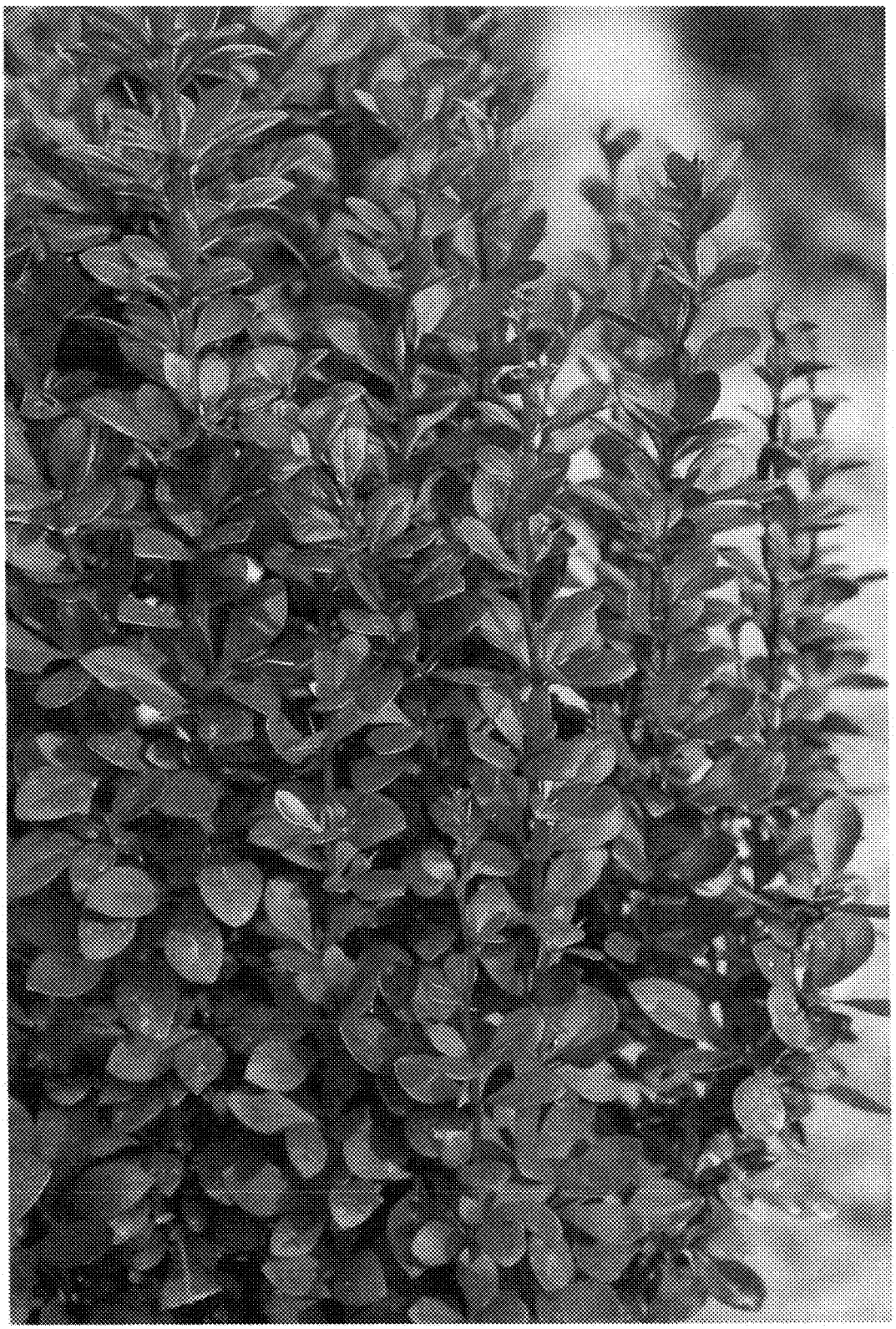

* * * * *